United States Patent [19]

Danby et al.

[11] Patent Number: 4,624,663
[45] Date of Patent: * Nov. 25, 1986

[54] PINCH VALVE ASSEMBLY

[75] Inventors: Hal C. Danby, Palo Alto; Carl Ritson, San Jose, both of Calif.

[73] Assignee: Critikon, Inc., San Jose, Calif.

[*] Notice: The portion of the term of this patent subsequent to Dec. 17, 2002 has been disclaimed.

[21] Appl. No.: 613,557

[22] Filed: May 24, 1984

Related U.S. Application Data

[63] Continuation-in-part of Ser. No. 493,182, May 10, 1983, Pat. No. 4,559,045.

[51] Int. Cl.⁴ ............................................. A61M 5/00
[52] U.S. Cl. ..................................... 604/250; 604/34; 251/7
[58] Field of Search ................... 604/250, 34; 251/7-9

[56] References Cited

U.S. PATENT DOCUMENTS

| | | | |
|---|---|---|---|
| 3,817,237 | 6/1974 | Bolouc | 604/250 X |
| 3,831,625 | 8/1974 | Roediger | 604/250 X |
| 3,915,167 | 10/1975 | Waterman | 604/250 |
| 4,300,552 | 12/1981 | Cannan | 604/250 X |
| 4,312,493 | 1/1982 | Stauffer | 604/250 X |
| 4,337,791 | 7/1982 | Tech et al. | 251/82 |
| 4,398,908 | 8/1983 | Siposs | 604/250 X |
| 4,493,710 | 1/1985 | King et al. | 604/250 |
| 4,559,045 | 12/1985 | Daney et al. | 604/250 |

Primary Examiner—Stephen C. Pellegrino
Attorney, Agent, or Firm—William B. Walker

[57] ABSTRACT

A disposable pinch valve assembly for parenteral solution delivery systems comprises a two-piece tubing receptor housing hingedly connected and with an irreversible snap connection which will not permit removal of the device from parenteral tubing after assembly. A back section has an integral movable pressure plate attached to the housing by integral flexible web connectors. When the movable plate is actuated toward the stationary press surface, tubing is pinched or crimped therebetween and the cross-section area of the flow passage through the tubing is reduced. The movable pressure plate is designed to engage a actuator connector which engages the device by turning the actuator by hand or by the use of a motor-driven actuator in an axially sliding engagement.

2 Claims, 23 Drawing Figures

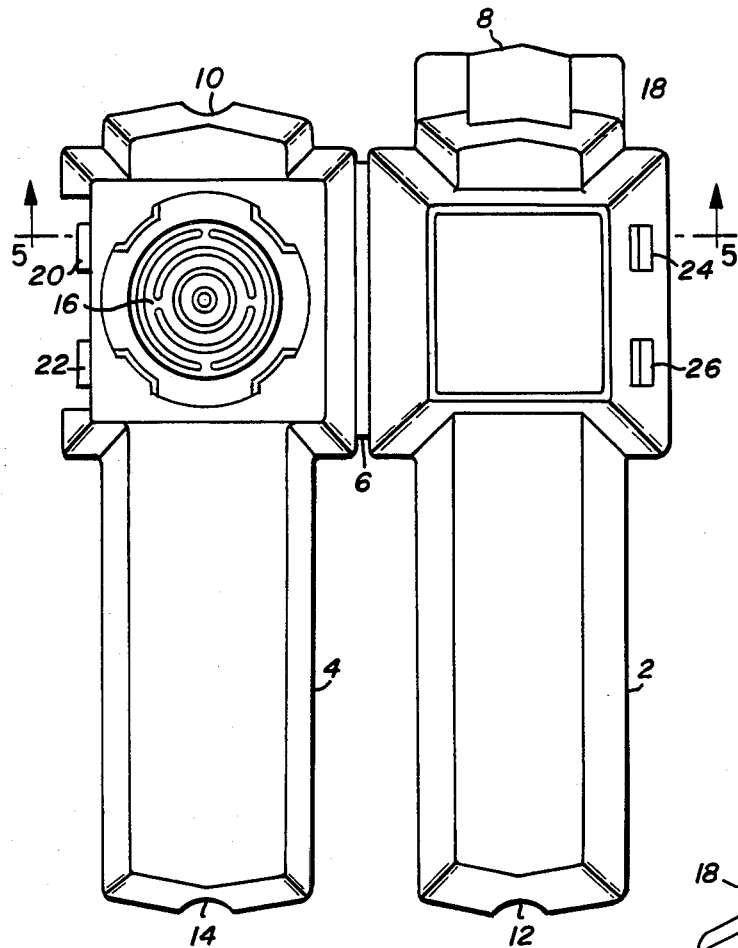
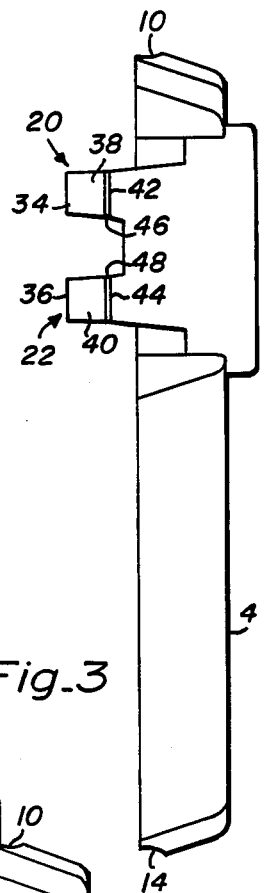
Fig_3
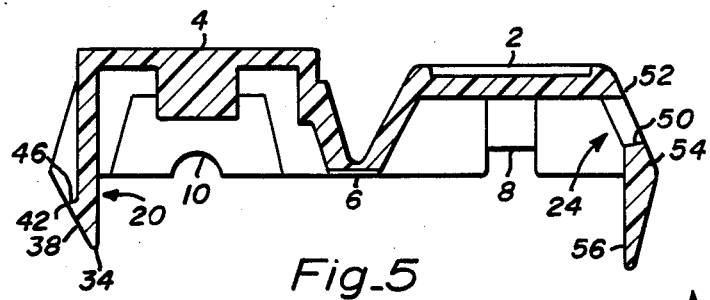
Fig_5
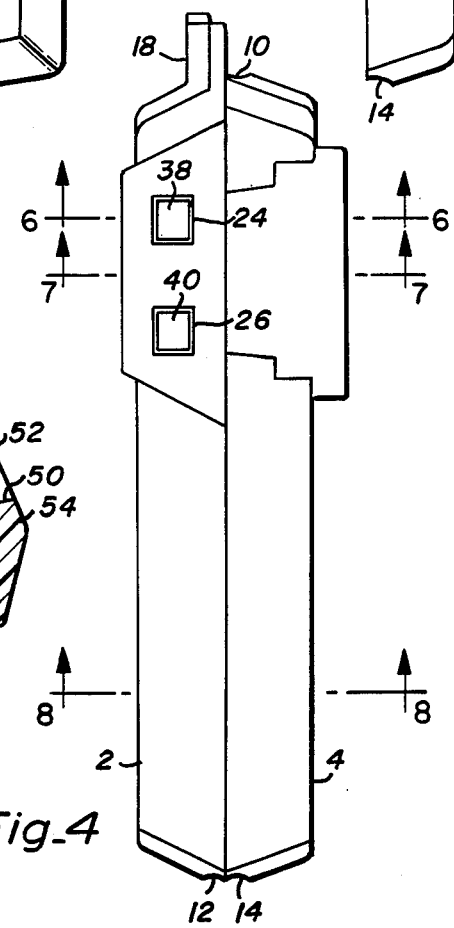
Fig_4
Fig_1

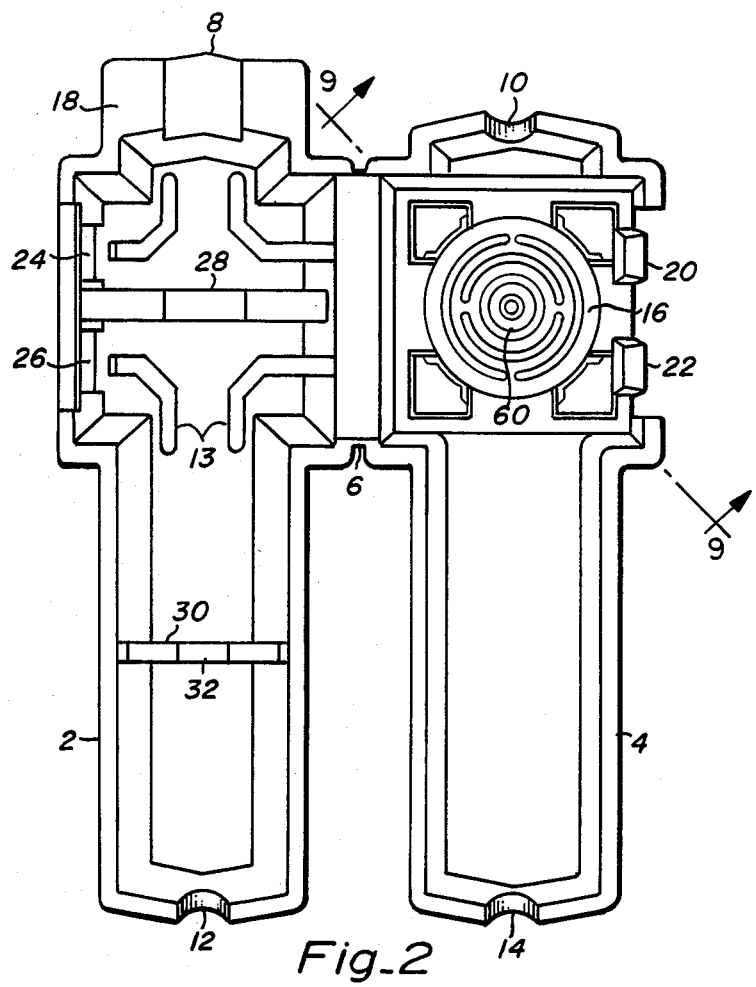
Fig_2
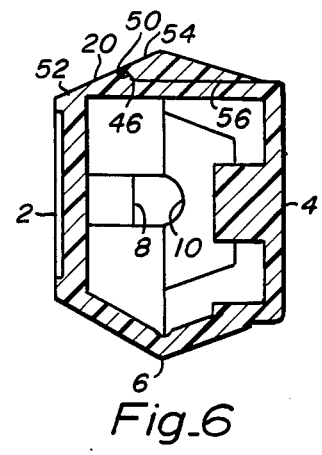
Fig_6
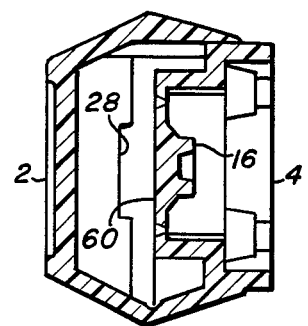
Fig_7
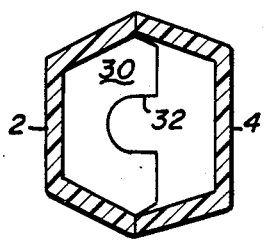
Fig_8
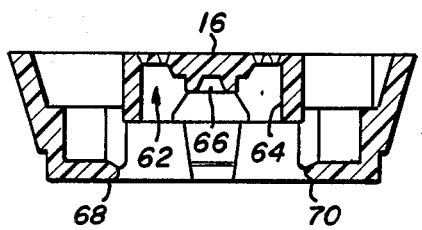
Fig_9
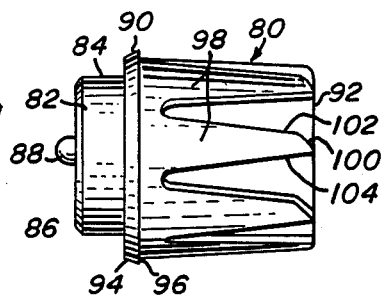
Fig_10

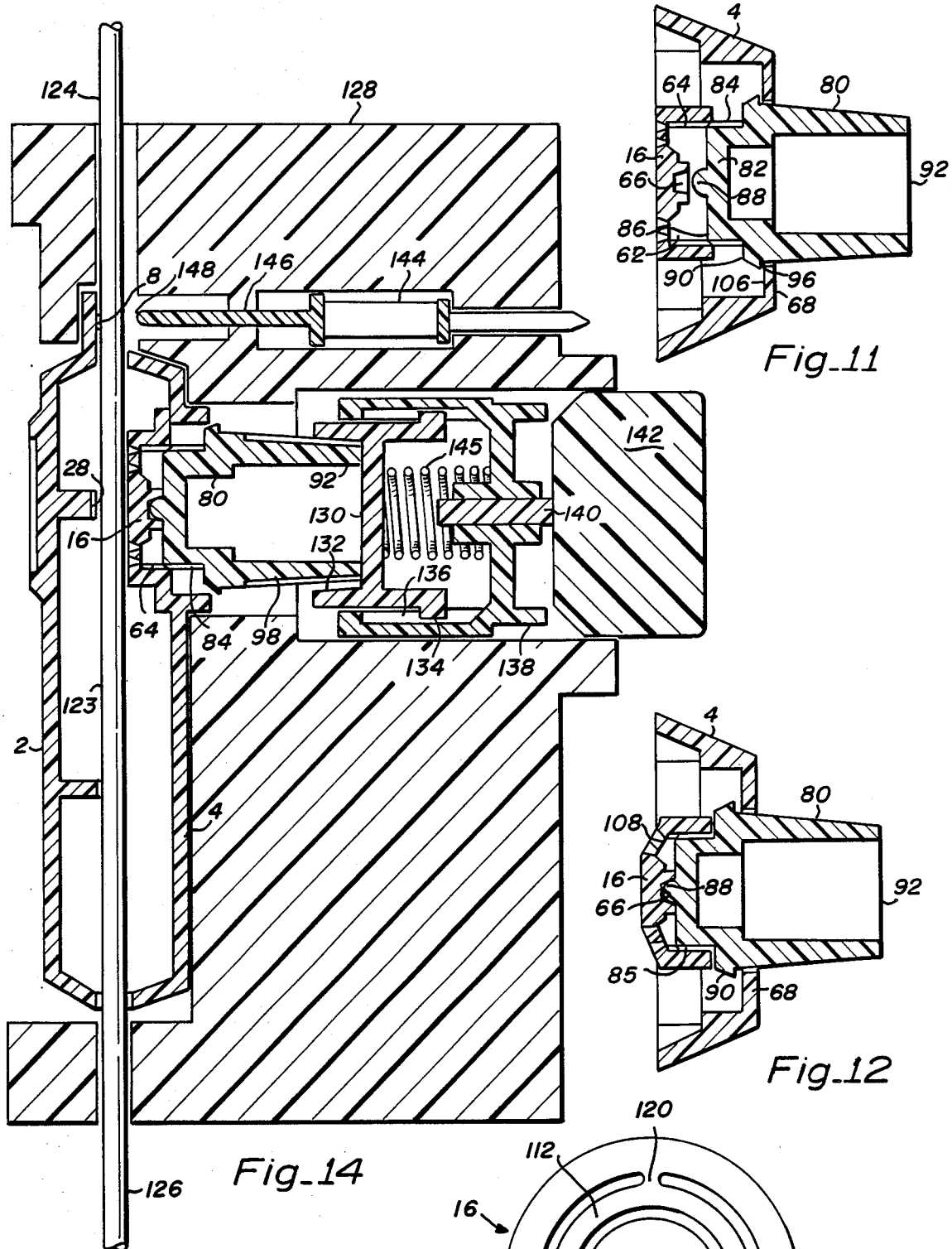

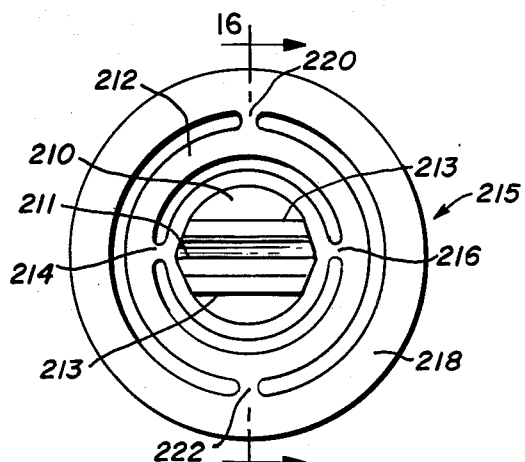
Fig_15
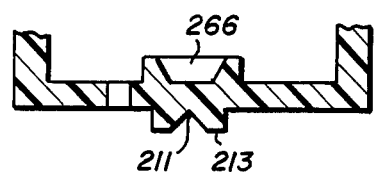
Fig_16
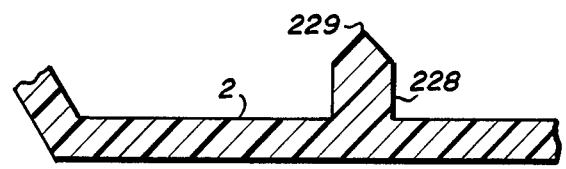
Fig_17
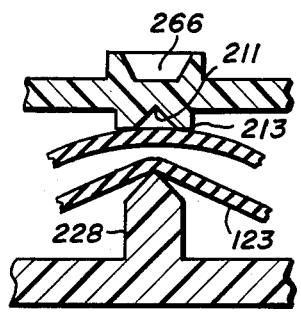
Fig_18
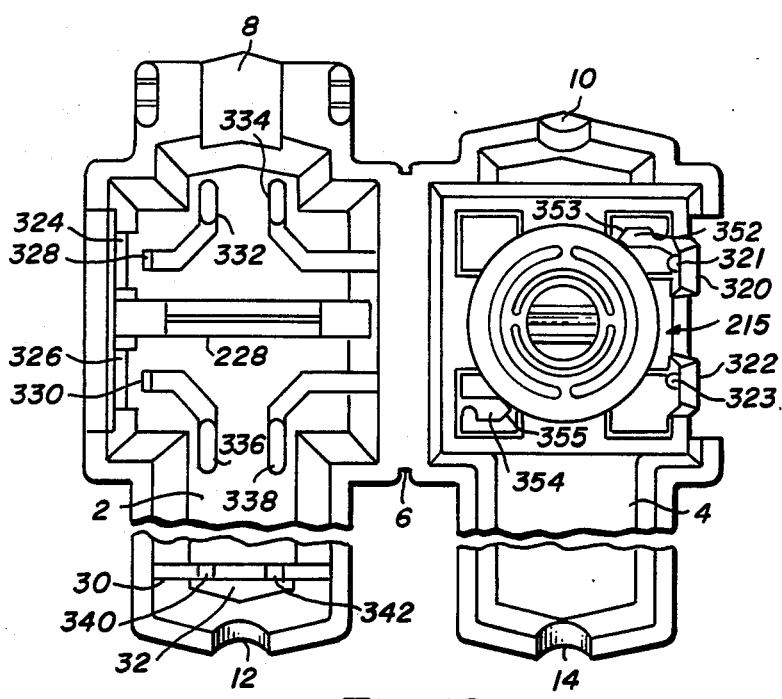
Fig_19

1

PINCH VALVE ASSEMBLY

RELATED APPLICATION

This is a continuation-in-part of application Ser. No. 493,182, filed May 10, 1983, now U.S. Pat. No. 4,559,045 the entire disclosure of which is incorporated herein by reference.

FIELD OF THE INVENTION

This invention relates to an apparatus for administering parenteral solutions to medical patients. In particular, this application is directed to an improved apparatus for delivering solutions at precise rates using a pinch valve flow control assembly.

BACKGROUND OF THE INVENTION
DESCRIPTION OF THE PRIOR ART

Infusion delivery systems for delivering liquid to a patient from more then one solution source have been previously known. The most common systems use gravity flow and manually adjustable tubing clamps or pinch valves. They may employ a variety of valves and junctions to control flow at the desired rate and sequence. Examples of such systems are described in U.S. Pat. Nos. 3,886,937; 4,034,754; 4,114,617; 4,219,002; 4,223,695; 4,236,515; 4,237,879; 4,237,880; 4,250,879; 4,252,116; 4,256,104; 4,256,105; and 4,258,712.

Automatic flow control systems relying on a drop counter which measures the frequency of drop fall through a drip chamber have been previously known. In general, a light beam from a lamp to a light detector is positioned so that it is interrupted by drops falling through a drip chamber. The frequency of the breaking of the light beam and/or the time lapse between drops breaking the light beam are directly proportional to the flow rate and are used to determine adjustments to be made to a flow control valve to change flow to the desired rate. Examples of systems comprising drop counters and control systems responsive thereto are described in U.S. Pat. Nos. 3,163,179; 3,601,124; 3,886,937; 4,038,982; 4,314,567.

The prior art pinch valve systems do not provide the precision and reliability needed to control flow rates.

SUMMARY AND OBJECTS OF THE INVENTION

It is an object of this invention to provide an inexpensive, disposable, pinch valve assembly suitable for use with automatic control systems capable of providing a highly precise flow rate of fluid to a patient.

The disposable pinch valve assembly of this invention is designed for use with parenteral solution delivery systems employing flexible tubing. It comprises a tubing receptor housing having a mutually engagable tubing support front section and back section engagable therewith. The front section includes a stationary pressure plate against which tubing can be pressed. The back section includes a movable pressure plate for pressing tubing against the stationary pressure plate to reduce the cross-sectional area of the flow passageway of the tubing. The movable plate is displaced in response to movement of a motor-driven actuator.

In one embodiment of the invention, the front section and back section are hingedly connected along one edge and have mutually engaging, irreversible connecting means on the opposite edge thereof. The movable plate means comprises a circular plate connected by flexible web connectors to an outer rim defined by the back section. The back section has a threaded recess for engagingly receiving an actuating connector. The actuating connector has a motor drive connector at one end and a threaded cylindrical actuator at the opposite end for engaging the threaded recess.

BRIEF SUMMARY OF THE DRAWINGS

FIG. 1 is a frontal view of the disposable pinch valve housing of this invention in the open position.

FIG. 2 is a back view of the disposable pinch valve housing of this invention in the open position.

FIG. 3 is a side view of the disposable pinch valve housing of this invention in the open position.

FIG. 4 is a side view of the disposable pinch valve housing of this invention in the closed position.

FIG. 5 is a cross-sectional view taken along the line 5—5 in the representation of the open pinch valve housing shown in FIG. 1.

FIG. 6 is a cross-sectional view taken along the line 6—6 in the representation of the closed pinch valve housing shown in FIG. 4.

FIG. 7 is a cross-sectional view taken along the line 7—7 in the representation of the closed pinch valve housing shown in FIG. 4.

FIG. 8 is a cross-sectional view taken along the line 8—8 in the representation of the closed pinch valve housing shown in FIG. 4.

FIG. 9 is a cross-sectional view taken along the line 9—9 in the representation of the pinch valve housing shown in FIG. 2.

FIG. 10 is a side view of the actuating connector of this invention.

FIG. 11 is a cross-sectional view showing the actuating connector assembled with the pinch valve housing in the initial assembly position.

FIG. 12 is a cross-sectional view showing the actuating connector assembled with the back housing section after actuating movement of the connector.

FIG. 13 is a representation of the back view of the movable plate showing the web construction.

FIG. 14 is a cross-sectional view of the disposable pinch valve assembly of this invention.

FIG. 15 is a representation of the back view of another embodiment of the movable plate.

FIG. 16 is a fragmentary cross-sectional view taken along the line 16—16 of the movable plate of FIG. 15.

FIG. 17 is a fragmentary view of another embodiment of the stationary pressure plate.

FIG. 18 is a fragmentary view showing the cooperation of the embodiment of the movable plate of FIG. 16 and stationary plate of FIG. 17 in a partially closed position.

FIG. 19 is a fragmentary back view of another embodiment of the disposable pinch valve of this invention in the open position.

DETAILED DESCRIPTION OF THE INVENTION

Figure 20:
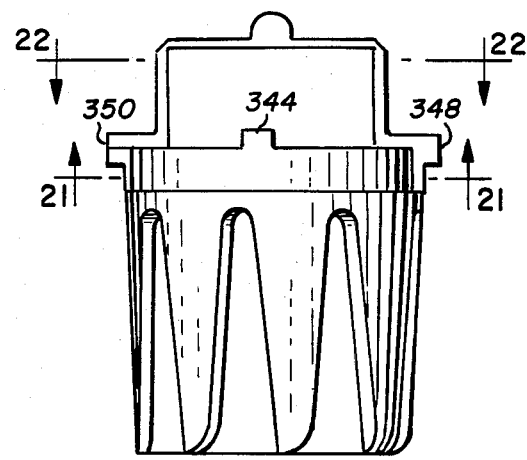
FIG. 20 is a side view of another embodiment of the acutating connector of this invention.
Figure 21:
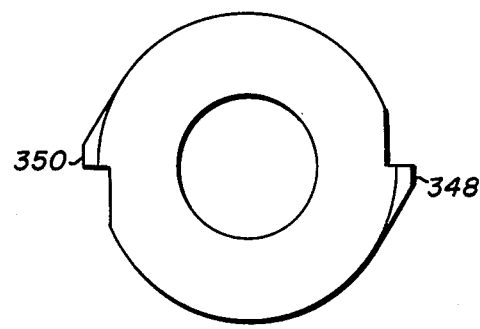
FIG. 21 is a cross-sectional view taken along the line 21—21 of the connector of FIG. 20.
Figure 22:
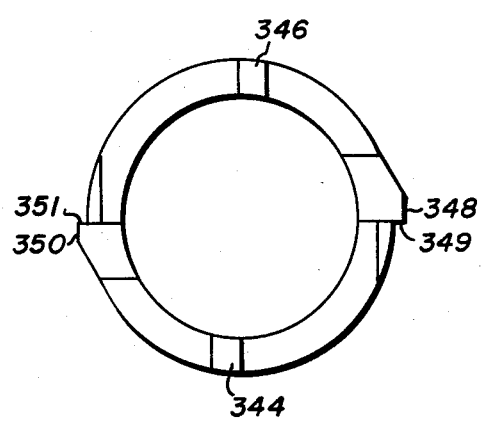
FIG. 22 is a cross-sectional view taken along the line 22 of the connector of FIG. 20.

Referring to FIGS. 1 and 2, the frontal and back views of the pinch valve housing in the open position are shown. The tubing receptacle housing comprises a front section 2 and a back section 4 joined by integral connecting hinge 6 along the common edge thereof. The tubing passes into the housing through the upper passageway defined by the stationary pressure plate 8 of the front section and upper tubing passageway 10 in the back section and exits between the lower passageway defined by the lower tubing passageway 12 in the front section and the lower tubing passageway 14 in the back section. The movable pressure plate 16 and connector webbing associated therewith are described in greater detail hereinafter with respect to FIGS. 11, 12 and 13. The latch projection 18 engages a retention latch described hereinafter with respect to FIG. 14. Snap connector means hold the front and back housing sections in irreversible engagement once they are closed into the mutually engaging position. The snap connector means comprises latch projections 20 and 22 of the receptor section and latch receptors 24 and 26 in the support section.

Referring to FIG. 2, the stationary pressure plate 28 has a flat surface transverse to the axis of the tubing passageways 8 and 12. The pressure plate 28 contributes a surface against which tubing can be pressed. The movable pressure plate 16 when advanced against tubing held between it and the stationary pressure plate 28 pinches the tubing, reducing the cross-sectional area of the passageway therethrough. The rate of liquid flow through the tubing can be controlled by regulating the distance between the movable and stationary pressure plates. The tubing support webbing 30 having a recess 32 which positions the tubing exactly between the passageways 8 and 12 and between the pressure plates 16 and 28 when the housing is closed around a tubing section.

FIG. 3 is a side view of the disposable pinch valve housing of this invention in the open position. The latch projections 20 and 22 have respective leading tips 34 and 36, including leading surfaces 38 and 40 which taper to projecting ribs or teeth 42 and 44 described in detail with regard to FIG. 5 hereinafter. The trailing surfaces 46 and 48 are critical for achieving an irreversible engagement of the housing in the closed position.

FIG. 4 is a side view of the disposable pinch valve assembly of this invention in the closed position. In this view the leading surfaces 38 and 40 of the latch projections 18 and 20 can be seen in the engaged position in the latch receptors 24 and 26.

FIG. 5 is a cross-sectional view taken along the line 5—5 in FIG. 1. Latch projection 20 can be seen to have a leading tip 34 and a rib or tooth 42 formed by the leading surface 38. This surface leads from the tip 34 to the edge of the tooth. The trailing surface 46 of the projection forms a sharp and preferably an acute angle with respect to the leading surface 38. The latch receptor 24 comprises an opening, the forward edge of which contributes a stop 50.

FIG. 6 is a cross-sectional view of the disposable pinch valve assembly of this invention in the closed position taken along the line 6—6 in FIG. 4. The latch projection 20 is made of flexible plastic and is deflected during a closure to pass by the housing surface 56. The projection 20 then resiliently returns to its unflexed orientation to snap into the opening of the latch receptor 24 (FIG. 5). Efforts to separate the housing are made difficult because the leading surface 38 of the latch projection 20 is flush with adjacent surfaces 52 and 54 of the front housing section 2. Furthermore, opening movement is prevented by the opposed surfaces of the trailing surface 46 and the stop 50. The hinge 60 provides a hinge binding action, full closure of the sections placing the hinge under tension. If closure is incomplete, this tension forces the front and back sections into a conspicuously open position, prompting the attendant to repeat the closure step until a complete closure is effected.

A critical function of this latch system is to prevent removal of this disposable pinch valve assembly from tubing once it is engaged in a fully functional way. This is an inexpensive disposable unit, and repeated use would risk loss of accurate control of flow rates. Therefore, it is critical that the latching mechanism prevent reuse.

FIG. 7 is a cross-sectional view of the disposable pinch valve assembly of this invention in the closed position taken along the line 7—7 in FIG. 4. The relative positions of the stationary pressure plate surface 28 and the movable pressure plate surface 60 can be seen. Tubing placed between the surfaces 28 and 60 can be squeezed by moving the movable pressure plate 16 in an axial direction towards the stationary pressure plate 28. As shown in FIG. 7, the stationary pressure plate 28 has two shoulders which receive the tubing therebetween and serve to prevent off center alignment and gimbaling action of the tubing.

FIG. 8 is a cross-sectional view of the disposable pinch valve assembly of this invention in a closed position taken along the line 8—8 in FIG. 4. In this drawing, the webbing 30 and tubing recess 32 is shown. This supports the tubing in a secure manner when engaging the two sections of the housing to maintain the tubing in a proper position between the movable pressure plate surface 60 and stationary pressure plate surface 28 until closure is complete.

FIG. 9 is a cross-sectional view of the pinch valve housing taken along the line 9—9 in FIG. 2. The actuating connector receptor recess 62 is a cylindrical recess having female threads 64. A recess 66 which engages the actuating connector after assembly is axially positioned in the center of the movable pressure plate 16. The retention snaps 68 and 70 function to retain the actuating connector means in position after assembly as described hereinafter with respect to FIGS. 11, 12 and 13.

FIG. 10 is a side view of the actuating connector 80. The actuating end of the actuating connector comprises a cylindrical connecting end 82 having male threads 84 and a leading surface 86 with an axially central projection 88. Annular flange 90 intermediate the connecting end 82 and the cylindrical motor drive connecting end 92 extends outwardly. The sloped leading surface 94 forms an acute angle with the trailing surface 96 for latching engagement with snap means 68 and 70 as shown in FIG. 9.

The motor connecting end of the actuating connector 80 comprises a cylinder which is axially aligned with the connector end 82. A plurality of splines 98 are formed in the outer surface of the cylinder surface. Each spline has a tip 100 which forms an obtuse angle with the trailing edge 102. The tip 100 forms an acute angle with the leading edge 104. The splines 98 join at their base in an acute angle. This configuration permits easy engagement with the female splines of the motor coupler shown in FIG. 14.

FIG. 11 is a cross-sectional view of the assembled back housing section 4 and the actuating connector 80. In this view, the connecting end 82 of the actuating connector 80 engaging the receptor recess 62. The projection 88 is positioned to engage the recess 66 in the movable pressure plate 16. The trailing surface 96 of the flange 90 engages the corresponding stop surface 106 of the retention snap 68 to retain the actuating connector securely in place after assembly. The distance between the leading face 86 and the trailing surface 96 of the actuating connector is insufficient to force the male threads 84 into engagement with the female threads 64. The actuating connector 80 can rotate freely after being assembled with the back housing section 4 without causing a premature engagement of the male threads 84 and female threads 64. This protects the movable pressure plate 16 and webbed connecting structure from stress and damage prior to actual use.

FIG. 12 is a cross-sectional view showing the actuator connector assembled with the back housing section after actuating movement of the connector. The forward actuating movement of the actuating connector 80 causes engagement 85 of the male threads 84 with the female threads 64 shown in FIG. 4. Rotation of the actuating connector 80 about its axis (in response to motor activation) causes advancement of the projection 88 and engagement with recess 66. Continued advancement displaces movable pressure plate 16 in an axial direction. Reverse rotation removes pressure on recess 66 permitting the movable pressure plate 16 to return toward its relaxed position, the webbing 108 providing the resiliency.

FIG. 13 is a detailed view of the movable pressure plate. The movable pressure plate 16 comprises the circular central plate 110. The circular ring 112 is connected to the central plate 110 by webs 114 and 116. The circular ring is attached to the outer rim 118 by means of webs 120 and 122. The webbing is constructed of flexible, resilient organic polymers and provides an elastic, flexible movement of the central plate 110 in an axial direction both toward and away from the stationary pressure plate 28.

FIG. 14 is a cross-sectional view of the fully assembled disposable pinch valve of this invention. The front section 2 and back section 4 of the pinch valve are closed on a suitably positioned flexible tubing 123, the tubing end 126 leading to the patient. The actuating connector 80 is assembled with the back section 4 of the pinch valve housing as shown in FIG. 11. The closed housing is then positioned in a recess in the motor housing 128.

The motor connector end 92 of the actuating connector 80 fits into the axially movable motor coupler 130, the splines 98 meshing with female projections 132 in a sliding engagement. The motor coupler 130 has male projections 134 which slide in grooves 136 in the coupling wheel 138. The coupling wheel is mounted on the drive shaft 140 of motor 142. Motor 142 can be any type of motor which can be controlled to move in preselected increments.

The spring 145 pushes the motor coupler and the actuating connector axially forward, and initial rotation of the coupling wheel 138 effects a threaded engagement of the threads 80 of the actuating connector 80 and threads 64 of the receptor recess. Continued rotation of wheel 138 advances the projection 88 and the movable pressure plate 16 toward the stationary prressure plate 28, reducing the cross-sectional area of the tubing passageway therebetween. Reverse rotation of wheel 138 reverses this axial movement in the direction away from the tubing, permitting the resilient tubing to return toward its relaxed configuration and increasing the cross-sectional area of the tubing passageway.

An additional safety feature is provided by the latch projection 18 on the front housing section 2. The rear surface 8 thereof functions as a stationary pressure plate. Actuation of the solenoid 144 drives the projection 146 against the tubing, the end 148 thereof tightly pinching the tubing against the surface 8. This completely closes the tubing, terminating fluid flow therethrough. The solenoid 144 can be automatically actuated in a manner known per se in the art in response to a system malfunction presenting risk to the patient.

FIGS. 15 and 16 show another embodiment of a movable plate for the practice of the present invention which differs with regard to the construction of the central plate 110 shown in the movable plate of FIG. 13.

The movable pressure plate 215 of FIG. 15 comprises a circular central plate 210 having a channel 211, defined at about a 45° angle, and pressure bars 213 which serve to press against the flexible tubing 123 as shown in FIG. 18. The circular ring 212 is connected to the central plate 210 by webs 214 and 216. The circular ring 212 is connected to the outer rim 218 by means of webs 220 and 222.

FIG. 16 is a fragmentary cross-sectional view along lines 16—16 of the movable plate of FIG. 15. This view shows the channel or grove 211 and pressure bars 213 which engage and press against the tubing 123 as the actuating connector 80 (see FIG. 11) engages the recess 266 in the movable plate 215.

FIG. 17 is a fragmentary view of the stationary pressure plate 228. In this embodiment, the stationary pressure plate has a peaked or point surface 229, defined at about 45° angle, which runs transverse to the axis of the tubing passageways 8 and 12. The pressure plate 228 provides a surface against which the tubing 123 can be pressed and crimped or bent. The movable pressure plate 215 when advanced against the tubing held between it and the stationary pressure plate 228, bends or crimps the tubing by reason of bars 213 and the pointed surface 229, thereby reduces the cross-sectional area of the passageway of the tube. This embodiment is particularly advantageous in that the amount of force or pressure required from the central plate 210 and actuator 80 in order to adjust the rate of liquid flow is very low.

FIG. 18 is a fragmentary cross-sectional view showing the cooperation of the movable pressure plate and the stationary pressure plate 228 wherein the flexible tubing 123 is only partially bent or crimped so that the rate of flow of liquid is only slightly diminished. The tubing is crimped along the axis established by the groove 211.

FIG. 19 is a fragmentary back view of another embodiment of the disposable pinch valve of this invention in the open position. In this embodiment is incorporated the movable plate embodiment of FIG. 15 and the stationary pressure plate embodiment of FIG. 17.

Referring to FIG. 19, the housing is provided with snap connector means comprising latch projections 320 and 322 of the back section 4, and latch receptors 324 and 326 of backstop posts 328 and 330 of the front section 2. The latch projections, as shown, are provided with ribs 321 and 323 which serve to provide firm and positive engagement of the latch projections with the posts 328 and 230 upon closing of the front and back sections. A critical function of the snap connector means is to prevent removal of the disposable pinch valve assembly from the tubing once it is engaged in a fully functional way. Upon closing of the front and back sections, the latch projections cannot be depressed because of the position of the rigid posts or stops 328 and 330. In this way, reuse of the assembly is prevented because it is not possible to open the assembly without breaking or destroying it. This is an inexpensive disposable unit and reuse would risk loss of accurate control of flow rates.

The front section 2, see FIG. 19, is provided with means for maintaining alignment of the tubing. The tubing alignment means comprises the posts 332,334; 336,338; and 340,342, each pair of which is spaced sufficiently to receive the tubing in friction engagement. Advantageously, the posts are rigid to slightly flexible plastic such as polypropylene with the upper part of the post curved inwardly and slightly over the upper curvature of the tubing in order to retain the tubing in place.

FIG. 20 is a side view of another embodiment of the actuating connector. This embodiment differs from the actuating connector 80 shown in FIG. 10 in that this embodiment is provided with depthstop means 344 and 346 and reverse direction shoulder stops 348 and 350. The depth stop permits the threading or screwing in of the connector to only a certain distance according to the height of the stops 344 and 346. The reverse direction shoulder stops 348 and 350 permit the clockwise turning of the actuating connector; however, in cooperation with the lugs 352 and 354 which project from the housing 4 (see FIG. 19), the counter clockwise turning of the actuating connector is prevented. The planar surface 349 and 351 of the shoulders 348 and 350, respectively, on counterclockwise turning of the actuating connector positively engage the planar surface 353 and 355, of the lugs 352 and 354, respectively, thereby preventing unthreading and disengagement of the actuating connector. The actuating connector 80 (FIG. 10) and the connector of FIG. 20 can be operated either by hand or through use of a motor.

Figure 23:
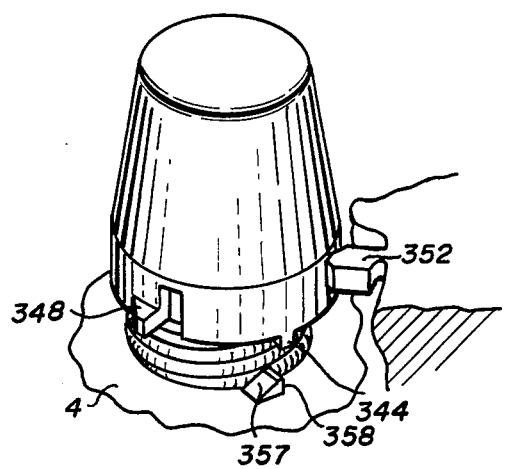
FIG. 23 is a perspective fragmentary view of the actuating connector of FIG. 20 in partial threaded engagement with the movable pressure plate showing in more detail the cooperation of the depth stop means of the connector and housing and the reverse direction control means of the connector and housing.

FIG. 23 is a perspective fragmentary view of the actuating connector embodiment of FIG. 20 shown in partial threaded engagement with the movable pressure plate 215 and its housing 4. This figure shows in more detail the depth stop means 344, 346 of the connector and 357, 359 of the housing 4 and the reverse rotation control means 348, 350 of the connector and 352, 354 of the housing 4. In addition, the planar surface of the depth stop means 344 will engage with the planar surface 358 of the depth stop means 357 so that clockwise rotation is prevented when the connector is threaded into the housing in substantially closed position. When the planar surfaces of depth stop means 348 and 357 (358) come into contact, further threading or closing of the connector is prevented. Because of this arrangement it is not possible to thread the connector completely into the housing. This has the advantage of reducing the effort or power necessary to turn the connector in a counterclockwise direction because of reduced surface friction and thereby minimize the chance of binding of the actuating connector and housing.

Various modifications of the present invention will be apparent to the person of ordinary skill in the art in view of the foregoing description and appended claims without departing from the spirit and scope of the invention. For example, the pointed support plate 228 and the channel member (211 and 213) can have their positions reversed so that the pointed support plate is an integral part of the movable support plate 215 and the channel member is used as the stationary support plate. All such modifications are included within the scope of the present invention.

The invention claimed is:

1. A disposable pinch valve assembly for a parenteral solution delivery system comprising a tubing receptor housing having mutually engagable front and back sections, the front section including a stationary pressure plate means against which tubing can be pressed, a motor driven actuator means, the back section including a movable pressure plate means for pressing tubing against said stationary pressure plate means in response to forward axial displacement by the motor-driven actuator means in threaded engagement therewith, the actuator means having a non-binding forward rotational depth stop means for stopping forward advancement of the actuating means beyond a position which represents total closure of the flow passageway of tubing positioned in the assembly, the non-binding depth stop means comprising planar surfaces of a housing projection and an actuator means projection which are positioned to abut when the forward axial displacement of the motor-driven actuator means advances to the position which represents total closure of the flow passageway of tubing positioned in the assembly.

2. A disposable pinch valve assembly for a parenteral solution delivery system comprising a tubing receptor housing having mutually engagable front and back sections, the front section including a stationary pressure plate means against which tubing can be pressed, a motor driven actuator means, the back section including a movable pressure plate means for pressing tubing against said stationary pressure plate means in response to forward axial displacement by the motor-driven actuator means in threaded engagement therewith, the actuating means having a non-binding reverse rotation stop means which prevents further reverse rotational movement of the actuating means when the actuator means is withdrawn to a position which represents a fully open flow passageway of tubing positioned in the assembly, the non-binding reverse rotation stop means comprising planar surfaces of a housing projection and an actuator means projection which are positioned to abut when the reverse axial displacement of the motor-driven actuator means withdraws to the position which represents a fully open flow passageway of tubing positioned in the assembly.

* * * * *